United States Patent [19]

Jones et al.

[11] Patent Number: 5,412,074
[45] Date of Patent: May 2, 1995

[54] SILCONE MODIFIED PROTEINS

[75] Inventors: Roger T. Jones, Cuddington; Mark A. Humphreys, Warrington, both of United Kingdom

[73] Assignee: Croda International PLC., United Kingdom

[21] Appl. No.: 971,023

[22] Filed: Nov. 2, 1992

[30] Foreign Application Priority Data

Nov. 1, 1991 [GB] United Kingdom ................. 9123251

[51] Int. Cl.$^6$ ............................................. A61K 47/48
[52] U.S. Cl. .................................... 530/353; 530/356; 530/357; 530/360; 530/375; 530/378; 530/408; 530/409; 530/410; 424/70.14
[58] Field of Search ............... 530/353, 356, 357, 360, 530/375, 378, 408, 409, 410; 514/21; 424/70

[56] References Cited

U.S. PATENT DOCUMENTS

| 4,280,992 | 7/1981 | Suguira et al. | 424/1 |
| 4,713,116 | 12/1987 | Krinski et al. | 530/370 X |
| 4,822,681 | 4/1989 | Schössler et al. | 428/405 |
| 4,894,468 | 1/1990 | Wilchek et al. | 530/417 X |
| 5,100,956 | 3/1992 | O'Lenick, Jr. | 530/406 X |

Primary Examiner—Michael G. Wityshyn
Assistant Examiner—C. Sayala
Attorney, Agent, or Firm—Lerner, David, Littenberg, Krumholz & Mentlik

[57] ABSTRACT

Organofunctional silicone chains having an organic moiety on at least one end of the chains, are covalently linked to free amino groups of proteins by the organic moieties to provide a useful ingredient for cosmetic formulations.

17 Claims, No Drawings

SILICONE MODIFIED PROTEINS

BACKGROUND OF THE INVENTION

The invention relates to certain new silicone modified proteins and to their use in cosmetics and toiletries.

The use of proteins, their hydrolysates and chemically modified derivatives in cosmetic formulations to provide performance and conditioning benefits to skin and hair is well known. These benefits derive mainly from the film-forming and moisture-retentive properties exhibited by such "cosmetic proteins" together with their substantivity (ability to adsorb and resist elution with water) to hair and skin.

Proteins from a variety of animal and vegetable sources can be used and the relative film-forming and moisture-retentive properties can be controlled by the selection of a particular protein and its average molecular weight. It is also possible to chemically modify proteins to modify their behavior and functionality. Examples include esterification of carboxyl groups, acylation of amino groups and quaternization of amino groups.

Benefits claimed for proteins and their derivatives in the conditioning of hair include improved combability, gloss, moisture control, body and reduced "fly-away". For skin, benefits include moisturization, skin-firming/smoothing, improved feel and anti-irritation effect.

Another category of conditioning agents which have established a significant role in cosmetics products are silicones. "Silicone" is a general term for a range of chemicals with different behavior and effects but characterized by the "silicon-oxygen silicone" chain. Polydimethylsiloxanes (dimethicones) exhibit low solubility in water, low surface tension and antifoam behavior and have been found to confer gloss and lubricity to hair and a soft feel to skin. To overcome the limitations of water insolubility, silicone glycols (dimethicone polyols) have been developed which also exhibit foaming behavior and confer lubricity to keratin substrates.

In order to provide substantivity to hair, amino functional silicones (e.g. amodimethycones) have been developed which are also capable of polymerizing on the hair, but are water insoluble.

From the foregoing it will be understood that "proteins" and "silicones" represent two distinct categories of valuable conditioning agents for skin and hair with different physical properties and functional benefits.

The possibility of developing modified proteins which would have some properties characteristic of silicones (e.g. increased lubricity) or alternatively silicones with some of the benefits of proteins (greater water solubility and substantivity), offers potential for the formulation of cosmetic products with novel properties.

Products which are mixtures of silicones and proteins have been offered but it will be obvious to those skilled in the art of cosmetic formulations that mixtures will not provide the desired improvement in solubility characteristics or substantivity and lubricity for rinse-off systems.

EP 0295 983 assigned to Exsymol SAM, describes products formed by the condensation of a silane, silanol or siloxane with the carboxylic acid group of amino acids. The products, which contain only one silicon atom per molecule, are claimed to have useful therapeutic and cosmetic effects.

SUMMARY OF THE INVENTION

It has now been discovered that silicone modified proteins can be made which can provide benefits both of proteins and of silicones. The combined benefits from both the protein and silicone components for the conditioning of skin or hair are not achievable from simple mixtures.

In accordance with the present invention, silicone modified proteins are provided of an organofunctional silicone chain having an organic moiety on at least one end, and a protein having a free amino group that is covalently linked to the silicone chain via the organic moiety.

The invention also relates to the use of the silicone modified proteins in cosmetics, especially but not exclusively for the treatment of skin and hair, and to cosmetic and other compositions comprising the silicone modified proteins.

DETAILED DESCRIPTION OF THE PREFERRED EMBODIMENT

The silicone modified proteins can be prepared by covalently attaching organofunctional silane/silicone compounds to the protein amino groups to form larger molecules. In addition, polymerization may occur through condensation of silanol groups resulting in cross-linking.

The protein may be derived from either animal or vegetable sources or by fermentation. It may be in the form of a chemically modified protein (for example quaternized) provided that some free amino groups are still present on the protein molecules.

As examples of existing cosmetic grade proteins we can cite collagen, elastin, keratin, casein, wheat, soya and silk. In this context the term "protein" is used to embrace both native and hydrolyzed proteins and no distinction is made between "protein" and polypeptides, peptides or peptones since these can all fall into the category of "hydrolyzed protein."

The average molecular weight of the "protein" may vary from about 500–500,000 Daltons but preferably within the range 500–50,000 Daltons and more preferably within the range 1,000–20,000 Daltons, expressed as weight average molecular weight derived from size exclusion chromatography.

It is necessary for the "protein" to be capable of solution in water or other suitable solvent or cosolvent (such as alcohols, propylene glycol, polyethylene glycols) to enable reaction to occur.

The organofunctional silicone used for reaction with the protein must contain a functional group capable of reacting with the chain terminal and/or side chain amino groups of the protein. Such reactive groups include acyl halide, sulphonyl halide, anhydride and epoxide functions. The "silicone" may comprise any compound containing a siloxane bond (Si—O—Si) or indeed any silane capable of forming a siloxane bond in situ by condensation (see Reaction 1) or, any alkoxysilanes which hydrolyze to form the respective silanols (see Reaction 2) then condense to form siloxane bonds (Reaction 1).

Reaction 1
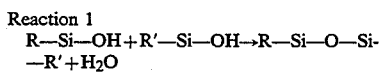

Reaction 2
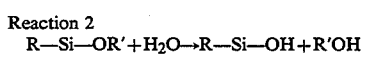

Examples of suitable organofunctional silicone/silane reagents include I–IV below:

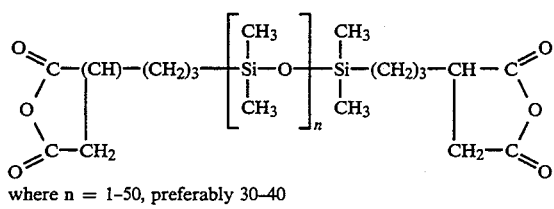

where n = 1–50, preferably 30–40

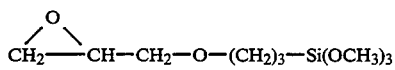

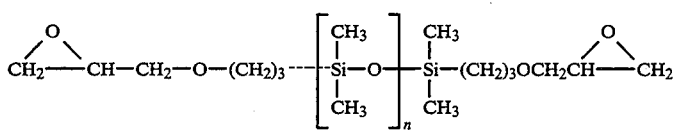

where n = 1–50, preferably 12–25

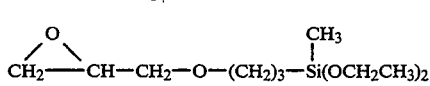

It will be understood that these molecules represent but a few illustrative examples of organofunctional silicones/silanes which can be used to produce desirable products and are not limitative of the present invention. Other molecules of a similar nature will suggest themselves, within the spirit and scope of the invention, to those skilled in the art of protein modification.

Preferably the organofunctional silicone/silane should be soluble in a solvent common to the protein for efficient reaction. The conditions for reaction of the organofunctional silicones/silanes with the protein to achieve the desired degree of reaction and cross-linking must be carefully controlled but will be apparent to those skilled in the art of protein modification and are not limitative to the present invention.

For reaction of the protein amino groups to occur, it is necessary for the pH of the system to be above pH 7 and preferably within the pH range 8–11.5. Reaction may occur at ambient temperature, but preferably at elevated temperature and more preferably within the range 40°–80° C.

The protein component of the silicone modified proteins may represent from 5% to 98% of the copolymer but more preferably 40–90% w/w.

The silicone modified proteins may be supplied as solutions in a suitable solvent, as dispersions or emulsions or as powder.

The chemical structures of the silicone modified proteins are complicated and the precise structure does not constitute a limitation of the present invention. Nevertheless, the silicone component may be illustrated by simplified structures V and VI below, depending upon whether the silicone constitutes a cross-link (V) or a chain attached to the protein at only one end (VI).

V

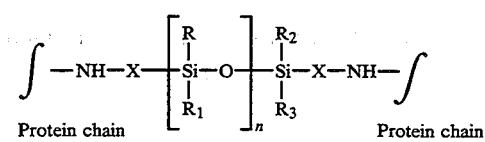

VI

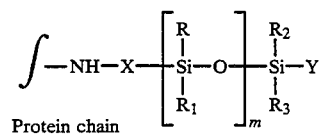

where:
(a) The "protein chain" represents a protein or hydrolyzed protein which may be chemically modified. Chemical modification may be performed prior or subsequent to production of the silicone modification of the protein.

The average molecular weight of the protein is in the range 500–500,000.

(b) X is the link group resulting from reaction of protein amino groups and the amino-reactive group on the organofunctional silicone/silane. Examples of X include, but are not limited to:

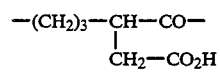

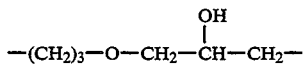

(c) R, R', $R_2$, $R_3$ may be —$CH_3$ or —OH.
(d) Y=OH or —X—OH
(e) n=1–50; m=0–50

It will be apparent that the silicone modified proteins may contain several silicone chains per protein molecule, depending upon the molecular weight of protein, the proportion of silicone to protein and the degree of cross-linking: such modified proteins can be characterized in terms of both chemical and physical properties by standard techniques and the degree of modification of protein amino groups and the protein and silicone contents determined.

The silicone modified proteins described have been found to exhibit physical and chemical properties which make them valuable for cosmetic products used for the conditioning of hair or skin. The properties vary with the composition of the protein and silicone components but specific benefits which have been found include: solubility in aqueous, aqueous/alcoholic or alcoholic solutions, film-forming characteristics, moisture retention, novel feel on skin, and excellent wet combing behavior on hair.

The inclusion of the silicone modified proteins into cosmetic formulations can be at any desired level but particularly useful are levels in the range 0.1-5% w/w.

The following non-limiting examples set forth hereinbelow illustrate certain aspects of the invention, but are not meant in any way to restrict the effective scope of the invention. It will be recognized that these give only an indication of the wide applicability and value of the silicone-modified proteins of the present invention in a range of cosmetic formulations. All parts and percentages are by weight unless otherwise noted, and all temperatures are in degrees Celsius.

EXAMPLES

Example 1

A silicone modified protein was prepared by reaction of an organofunctional silane with hydrolyzed collagen protein having a weight average molecular weight of approximately 5,000 daltons. The product had the general structure illustrated in V and VI where:

$R = CH_3$ $R_1 = OH$ $R_2 = CH_3$ $R_3 = OH$ $$X = (CH_2)_3-O-CH_2-\overset{\underset{|}{OH}}{C}H-CH_2-$$

$Y = OH$ $n = 1, m = 0$

The degree of modification of the protein amino group was 48% and the protein content was 90%. The product was significantly more viscous than the original collagen hydrolysate at equivalent concentration, as indicated by the figures below:

|  | Viscosity at 25%, 25° C. |
|---|---|
| Hydrolyzed Collagen | 30 mps |
| Silicone Modified Collagen | 500 mps |

The product was soluble in water and 50/50 alcohol-water.

When applied as a solution to a glass-slide and dried, the silicone modified collagen produced a hard, glossy, (non-tacky) film. Applied to the skin as a 5% solution, it exhibited characteristic "tack" of hydrolyzed collagen, but with a pleasing lubricating feel and when dry conferred a smooth feel to the skin. When a hair swatch was treated by immersing it in a 2% solution of the product for 30 seconds followed by rinsing with water, the hair exhibited excellent wet-combing behavior when compared with a water-control. Radiolabelling studies of substantivity to hair showed that the product exhibited behavior characteristic of proteins.

Example 2

A silicone modified protein was prepared by reaction of an organofunctional silane with hydrolyzed wheat protein having a weight average molecular weight of approximately 10,000 daltons. The product had the general structure illustrated in V and VI where:

$R = OH$ $R_1 = OH$ $R_2 = OH$ $R_3 = OH$ $$X = (CH_2)_3-O-CH_2-\overset{\underset{|}{OH}}{C}H-CH_2,$$

$n = 1, m = 0$

The degree of modification of the protein amino groups was 60%. The remaining amino groups were then quaternized to attach lauryl dimethyl quat groups to the protein, bringing the total modifications of amino groups to 85%.

The resultant silicone modified protein (quaternized) exhibited inverse solubility in water. That is, it was more soluble at high active concentrations in water than at low active concentrations. The effect was very pH dependent. At pH 7, a haze developed at concentrations below approximately 10% concentration; at pH 4.5 the haze point was at approximately 20% concentration; at pH 9 the haze point was at approximately 1% concentration.

The viscosity of the product was significantly increased compared with the starting wheat protein at equivalent concentrations as indicated below:

|  | Viscosity at 27% w/w, 25° C. |
|---|---|
| Wheat Protein | 40 mps |
| Silicone Modified Wheat Protein | 680 mps |

The product was soluble in anionic surfactants. For example, 6% sodium lauryl ether sulphate containing 2% active silicone modified wheat protein at pH 7 was a clear solution.

Substantivity tests performed on hair, using radiolabelled product showed that the product was substantive to hair from this anionic shampoo system. Hair swatches treated in this way exhibited improved wet combability and general manageability.

Example 3

A silicone modified protein was prepared by reaction of an organofunctional silicone with an ethyl ester of hydrolyzed collagen having a weight average molecular weight of approximately 4,000 daltons. The product had the general structure illustrated in V and VI where:

$R = CH_3$ $R_1 = CH_3$ $R_2 = CH_3$ $R_3 = CH_3$

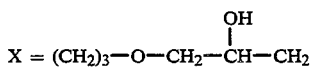

n = 12

The reaction procedure was as follows:

90 g ethyl ester of hydrolyzed collagen dissolved in 210 g absolute ethanol were placed in a 1 liter glass reaction vessel fitted with a stirrer and a reflux condenser. The temperature was increased to 70° C. using a water-bath and the pH adjusted to 11.0 with solid sodium hydroxide. 108 g of organofunctional silane (see III where n=12) were added and the temperature and pH maintained at 70° C. and pH 11.0 respectively overnight. The pH was then reduced by addition of concentrated sulphuric acid to pH 6 and the solution filtered to give a solution of silicone modified collagen.

The product contained 45% protein and 70% of the amino groups had been modified.

The alcohol-soluble product is useful for hair sprays, providing a glossy film on the hair. It is insoluble in water and precipitates from alcoholic solution on addition of water.

Example 4

A silicone modified protein was prepared by reaction of an organofunctional silane with hydrolyzed wheat protein having a weight average molecular weight of approximately 3,500 Daltons. The product had the general structure illustrated in V and VI, where:

R = OH $R_1 = CH_3$ $R_2 = OH$ $R_3 = CH_3$

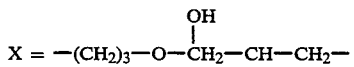

Y = OH n = 1, m = 0

The degree of modification of the protein amino groups was 82% and the protein content was 50%.

The viscosity of the modified protein, measured at 27% w/w concentration, 25° C. was 400 mps, which represented a substantial increase over the viscosity of the parent protein hydrolysate, due to cross-linking.

The modified protein exhibited inverse solubility in water in the pH region below approximately pH 6.

On drying a solution of the modified protein to form a constant weight film at 25° C., 40% RH, additional cross-linking occurred so that the modified protein could be only partially re-solubilized in pH 7 buffer at 25° C.; the film having a pH of 7 could only be redissolved to the extent of 67%. Film having a pH of 7 could only be redissolved to the extent of 62%. In contrast, control films of the parent wheat protein hydrolysate dissolved completely and much more rapidly.

Hair swatches were treated with 3% active solutions of the modified protein at pH 7 and then rinsed with water. The wet combability was assessed by eight panellists, in comparison with tresses similarly treated with the parent hydrolyzed wheat protein. The hair tresses were subsequently dried and assessed for dry combability. The tresses treated with the modified protein were found to be significantly better on both wet and dry combability than the control tresses treated with the wheat protein hydrolysate.

1% of the modified protein was added to a conventional shampoo formulation which was used to treat hair tresses. The contact time was 10 minutes, after which the tresses were thoroughly rinsed with water and dried. Control tresses were treated with the same shampoo containing no modified proteins.

24 panellists assessed the hair tresses for feel, shine and dry-combing behavior. Tresses treated with shampoo containing the modified protein were scored higher than the control tresses in terms of feel, shine and dry-combability.

As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A silicone modified protein comprising:
   an organofunctional silicone chain having a first end and a second end;
   a first organic moiety on said first end of said chain and a second organic moiety on said second end of said chain; and
   a first protein having a free amino group covalently linked to said silicone chain via said first organic moiety and a second protein having a free amino group covalently linked to said silicone chain via said second organic moiety.

2. The silicone modified protein of claim 1, wherein said silicone chain comprises one or more moieties independently selected from the group consisting of siloxane moieties, silane moieties and alkoxysilane moieties capable of hydrolyzing to form silanol moieties, wherein said silane and silanol moieties are capable of forming a siloxane moiety in situ by condensation.

3. The silicone modified protein of claim 1, wherein said first and second organic moieties are selected from the group consisting of acyl halide, sulphonyl halide, acid anhydride and epoxide moieties.

4. The silicone modified protein of claim 1, wherein said first and second proteins are derived from an animal, vegetable or fermentation source.

5. The silicone modified protein of claim 1, wherein said first and second proteins are selected from the group consisting of collagen, elastin, keratin, casein, wheat, soya and silk proteins.

6. The silicone modified protein of claim 1, wherein said first and second proteins comprise a hydrolyzed protein.

7. The silicone modified protein of claim 1, wherein said first and second proteins comprise at least one esterified carboxylic acid group or an acylated or quaternized amino group other than said free amino group.

8. The silicone modified protein of claim 1, wherein said first and second proteins have a weight average molecular weight between about 500 and about 500,000 daltons.

9. The silicone modified protein of claim 8, wherein said weight average molecular weight is between about 500 and 50,000 daltons.

10. The silicone modified protein of claim 9, wherein said weight average molecular weight is between about 1,000 and about 20,000 daltons.

11. The silicone modified protein of claim 1, wherein said first and second proteins comprise a plurality of free amino groups covalently linked to a plurality of organofunctional silicone chains via organic moieties.

12. The silicone modified protein of claim 1, wherein said second protein comprises a plurality of free amino groups covalently linked to a plurality of organofunctional silicone chains via organic moieties.

13. The silicone modified protein of claim 1, comprising from about 5% to about 98% protein by weight.

14. The silicone modified protein of claim 13, comprising from about 40% to about 90% protein by weight.

15. A cosmetic composition comprising from about 0.1% to about 10% by weight of the silicone modified protein of claim 1.

16. A shampoo composition comprising a surfactant and from about 0.1% to about 10% by weight of the silicone modified protein of claim 1.

17. The shampoo composition of claim 16, wherein said surfactant comprises an anionic surfactant.

* * * * *

UNITED STATES PATENT AND TRADEMARK OFFICE
CERTIFICATE OF CORRECTION

PATENT NO.   :   5,412,074
DATED        :   May 2, 1995
INVENTOR(S)  :   Jones et al.

It is certified that error appears in the above-identified patent and that said Letters Patent is hereby corrected as shown below:

On the title page, [54] "SILCONE" should read --SILICONE--.

Column 3, lines 22-26, after "where n = 50, preferably 12-25", skip one line, and insert at the right margin before the formula --IV--.

Column 4, lines 1-30: line 1, delete "VI" and just above the formula (lines 24-30), insert at the right margin --VI--.

Column 6, line 18, after "-CH$_2$," insert --Y=OH--.

Signed and Sealed this

Fifth Day of September, 1995

*Attest:*

BRUCE LEHMAN

*Attesting Officer*   Commissioner of Patents and Trademarks